US00PP17460P2

(12) United States Plant Patent
Wain

(10) Patent No.: US PP17,460 P2
(45) Date of Patent: Feb. 27, 2007

(54) ***CHRYSANTHEMUM* PLANT NAMED 'YOSUN CITY'**

(50) Latin Name: *Chrysanthemum×morifolium*
Varietal Denomination: Yosun City

(75) Inventor: Peter Wain, Locks Heath (GB)

(73) Assignee: Yoder Brothers, Inc., Barberton, OH (US)

( * ) Notice: Subject to any disclaimer, the term of this patent is extended or adjusted under 35 U.S.C. 154(b) by 30 days.

(21) Appl. No.: 11/157,432

(22) Filed: Jun. 21, 2005

(51) Int. Cl.
*A01H 5/00* (2006.01)

(52) U.S. Cl. ..... Plt./286
(58) Field of Classification Search ..... Plt./286
See application file for complete search history.

*Primary Examiner*—Kent Bell
(74) *Attorney, Agent, or Firm*—C. A. Whealy

(57) ABSTRACT

A new and distinct cultivar of *Chrysanthemum* plant named 'Yosun City', characterized by its uniform and somewhat outwardly spreading plant habit; strong and freely branching growth habit; dark green-colored foliage; uniform flowering response and habit; typically grown as a spray-type; early flowering habit; large daisy-type inflorescences with elongated oblong-shaped ray florets; red and yellow bi-colored ray florets; and excellent postproduction longevity with plants maintaining good substance and color for about four weeks in an interior environment.

2 Drawing Sheets

Botanical designation: *Chrysanthemum×morifolium.*
Cultivar denomination: 'Yosun City'.

BACKGROUND OF THE INVENTION

The present Invention relates to a new and distinct cultivar of *Chrysanthemum* plant, botanically known as *Chrysanthemum×morifolium* and hereinafter referred to by the name 'Yosun City'.

The new *Chrysanthemum* is a product of a planned breeding program conducted by the Inventor in Fareham, Hampshire, United Kingdom. The objective of the program is to create or discover new potted *Chrysanthemum* cultivars that are suitable for year-round production with uniform plant growth habit, good vigor and strong branching habit, numerous inflorescences, desirable inflorescence form and floret colors, fast and uniform flowering response, and good postproduction longevity.

The new *Chrysanthemum* originated from a cross-pollination made in January, 2001 in Fareham, Hampshire, United Kingdom, of a proprietary selection of *Chrysanthemum×morifolium* identified as code number P130E 1, not patented, as the female, or seed, parent with the *Chrysanthemum×morifolium* cultivar Los Alamos, not patented, as the male, or pollen, parent. The new *Chrysanthemum* was discovered and selected by the Inventor as a single flowering plant within the progeny of the stated cross-pollination grown in a controlled environment in Fareham, Hampshire, United Kingdom in January, 2001. The selection of this plant was based on its uniform plant growth habit, good vigor and strong branching habit, desirable inflorescence form and floret colors, fast and uniform flowering response, and good postproduction longevity.

Asexual reproduction of the new *Chrysanthemum* by vegetative tip cuttings was first conducted in Fareham, Hampshire, United Kingdom in January, 2001. Asexual reproduction by cuttings has shown that the unique features of this new *Chrysanthemum* are stable and reproduced true to type in successive generations.

SUMMARY OF THE INVENTION

The cultivar Yosun City has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Yosun City'. These characteristics in combination distinguish 'Yosun City' as a new and distinct *Chrysanthemum:*

1. Uniform and somewhat outwardly spreading plant habit.
2. Strong and freely branching growth habit.
3. Dark green-colored foliage.
4. Uniform flowering response and habit.
5. Typically grown as a spray-type.
6. Early flowering, eight week response time.
7. Large daisy-type inflorescences with elongated oblong-shaped ray florets.
8. Red and yellow bi-colored ray florets.
9. Excellent postproduction longevity with plants maintaining good substance and color for about four weeks in an interior environment.

Plants of the new *Chrysanthemum* can be compared to plants of the female parent selection. Plants of the new *Chrysanthemum* differ from plants of the female parent selection primarily in ray floret color as plants of the female parent selection have red-colored ray florets. In addition, plants of the new *Chrysanthemum* flowered about three or four days later than plants of the female parent selection.

Plants of the new *Chrysanthemum* can be compared to plants of the male parent, the cultivar Los Alamos. Plants of the new *Chrysanthemum* differ from plants of the cultivar Los Alamos in the following characteristics:

1. Plants of the new *Chrysanthemum* are larger than plants of the cultivar Los Alamos.
2. Plants of the new *Chrysanthemum* have larger inflorescences than plants of the cultivar Los Alamos.
3. Plants of the new *Chrysanthemum* flower about three to four days earlier than plants of the cultivar Los Alamos.

Plants of the new *Chrysanthemum* can be compared to plants of the cultivar Yobaton Rouge, disclosed in U.S. Plant Pat. No. 11,283. In side-by-side comparisons conducted in Fareham, Hampshire, United Kingdom, plants of the new *Chrysanthemum* differed from plants of the cultivar Yobaton Rouge in the following characteristics:

1. Plants of the new *Chrysanthemum* were larger than plants of the cultivar Yobaton Rouge.
2. Plants of the new *Chrysanthemum* had larger inflorescences than plants of the cultivar Yobaton Rouge.
3. Plants of the new *Chrysanthemum* flowered about three to four days earlier than plants of the cultivar Yobaton Rouge.

Plants of the new *Chrysanthemum* can also be compared to plants of the cultivar Cedar Falls, disclosed in U.S. Plant Pat. No. 13,068. In side-by-side comparisons conducted in Fareham, Hampshire, United Kingdom, plants of the new *Chrysanthemum* differed from plants of the cultivar Cedar Falls in the following characteristics:

1. Plants of the new *Chrysanthemum* were shorter than plants of the cultivar Cedar Falls.
2. Plants of the new *Chrysanthemum* had more pointed ray florets than plants of the cultivar Cedar Falls.
3. Plants of the new *Chrysanthemum* flowered about one week earlier than plants of the cultivar Cedar Falls.

BRIEF DESCRIPTION OF THE PHOTOGRAPHS

The accompanying colored photographs illustrate the overall appearance of the new *Chrysanthemum* showing the colors as true as it is reasonably possible to obtain in colored reproductions of this type. Colors in the photographs may differ from the color values cited in the detailed botanical description which accurately describe the colors of the new *Chrysanthemum.*

The photograph on the first sheet comprises a side perspective view of typical flowering plants of 'Yosun City' grown as spray-types.

The photograph on the second sheet comprises a close-up view of typical inflorescences of 'Yosun City' grown as spray-types.

DETAILED BOTANICAL DESCRIPTION

In the following description, color references are made to The Royal Horticultural Society Colour Chart, 1995 Edition, except where general terms of ordinary dictionary significance are used. The aforementioned photographs, following observations and measurements describe plants grown and flowered during the spring in Salinas, Calif., in a fiberglass-covered greenhouse and under conditions which approximate those generally used in commercial potted *Chrysanthemum* production. During the production of these plants, the following conditions were measured: day temperatures, 21 to 27° C.; night temperatures, 17 to 19° C.; and light levels, 5,000 to 6,000 foot-candles. Four unrooted cuttings were directly stuck in 15-cm containers, exposed to long day/short night conditions, and pinched once about two weeks later. At the time of the pinch, the photoinductive short day/long night treatments were initiated. Plants used for the description were grown as spray-types. Measurements and numerical values represent averages of typical flowering plants.

Botanical classification: *Chrysanthemum×morifolium* cultivar Yosun City.

Commercial classification: Daisy-type potted *Chrysanthemum.*

Parentage:

*Female, or seed, parent.*—Proprietary selection of *Chrysanthemum×morifolium* identified as code number P130E 1, not patented.

*Male, or pollen, parent.*—*Chrysanthemum×morifolium* cultivar Los Alamos, not patented.

Propagation:

*Type.*—Terminal tip cuttings.

*Time to initiate roots.*—About four days at 21° C.

*Time to produce a rooted cutting.*—About ten days at 21° C.

*Root description.*—Fibrous; white, close to 155D, in color.

*Rooting habit.*—Freely branching; moderately dense.

Plant description:

*Appearance.*—Herbaceous daisy-type potted *Chrysanthemum* that is typically grown as a spray-type. Upright with lateral branches somewhat outwardly spreading; uniformly mounded crown. Strong and freely branching growth habit; about four lateral branches develop after removal of terminal apex (pinching); dense and full plants.

*Plant height.*—About 28 cm.

*Plant width.*—About 41 cm.

*Lateral branches.*—Length: About 23 cm. Diameter: About 4 mm. Internode length: About 2.8 cm. Strength: Strong. Texture: Pubescent. Color: Close to 146A.

*Foliage description.*—Arrangement: Alternate; simple. Length: About 8.4 cm. Width: About 6.75 cm. Apex: Mucronate. Base: Mostly truncate. Margin: Palmately lobed, sinuses between lateral lobes mostly divergent. Texture, upper and lower surfaces: Pubescent. Color: Developing and fully expanded foliage, upper surface: Darker green than 147A. Developing and fully expanded foliage, lower surface: Close to 147A. Venation, upper surface: Close to 147A. Venation, lower surface: Close to 146A. Petiole length: About 2.2 cm. Petiole diameter: About 3 mm. Petiole texture, upper and lower surfaces: Pubescent. Petiole color, upper surface: Close to 146A. Petiole color, lower surface: 146A to 146B.

Inflorescence description:

*Appearance.*—Daisy-type inflorescence form with elongated oblong-shaped ray florets. Inflorescences borne on terminals above foliage. Disk and ray florets develop acropetally on a capitulum. Inflorescences not fragrant.

*Flowering response.*—Under natural conditions, plants flower in the autumn/winter in the Northern Hemisphere. At other times of the year, inflorescence initiation and development can be induced under short day/long night conditions (at least 13.5 hours of darkness). Uniform and early flowering habit; plants exposed to two weeks of long day/short night conditions followed by photoinductive short day/long night conditions flower about eight weeks later.

*Postproduction longevity.*—Inflorescences maintain good color and substance for about four weeks in an interior environment.

*Quantity of inflorescences.*—Grown as a spray-type, about nine per lateral branch.

*Inflorescence bud.*—Height: About 7.5 mm. Diameter: About 8 mm. Shape: Oblate. Color: Close to 146A.

*Inflorescence diameter.*—Large, about 8.5 cm.

*Inflorescence height.*—About 3.2 cm.

*Diameter of disc.*—About 1.4 cm.

*Receptacle diameter.*—About 6.5 mm.

*Receptacle height.*—About 5.5 mm.

*Ray florets.*—Length: About 4.8 cm. Width: About 1 cm. Corolla tube length: About 7 mm. Shape: Elongated oblong. Apex: Acute to emarginate. Base: Fused into a corolla tube. Margin: Entire. Orientation: Initially upright to eventually reflexing. Texture, upper and lower surfaces: Smooth, glabrous; velvety. Number of ray florets per inflorescence: About 22 arranged in a single whorl. Color: When opening and fully opened, upper surface: Center, 46A; towards the base and margins, 9A, with random spots and streaks, 46A. When opening and fully opened, lower surface: Close to 6A to 6C underlain with close to 59A.

*Disc florets.*—Arrangement: Massed at center of receptacle. Length: About 8 mm. Diameter, apex: About 2.5 mm. Diameter, base: About 1.5 mm. Shape: Tubular; elongated. Apex: Five-pointed. Number of disc florets per inflorescence: About 92. Color: Immature: Close to 154B. Mature, apex: Close to 9A. Mature, mid-section: Close to 145C. Mature, base: Close to 155D.

*Phyllaries.*—Quantity per inflorescence: About 24 arranged in about two to three whorls. Length: About 9 mm. Width: About 3 mm. Shape: Lanceolate. Apex: Acute. Base: Truncate. Margin: Entire. Texture, upper surface: Waxy, smooth. Texture, lower surface: Pubescent. Color, upper surface: Close to 144A. Color, lower surface: Close to 146A.

*Peduncles.*—Length, terminal peduncle: About 3.2 cm. Length, fourth peduncle: About 4.7 cm. Length, seventh peduncle: About 4.7 cm. Diameter: About 3 mm. Strength: Strong. Texture: Pubescent. Angle: About 45° from vertical. Color: Close to 146A.

*Reproductive organs.*—Androecium: Present on disc florets only. Anther length: Less than 1 mm. Anther color: Close to 9A. Pollen amount: None observed. Gynoecium: Present on both ray and disc florets. Style length: About 6 mm. Style color: Close to 155A. Stigma color: Close to 9A.

*Seed/fruit.*—Seed and fruit production has not been observed.

Disease/pest resistance: Resistance to pathogens and pests common to *Chrysanthemums* has not been observed on plants grown under commercial greenhouse conditions.

It is claimed:

1. A new and distinct cultivar of *Chrysanthemum* plant named 'Yosun City', as illustrated and described.

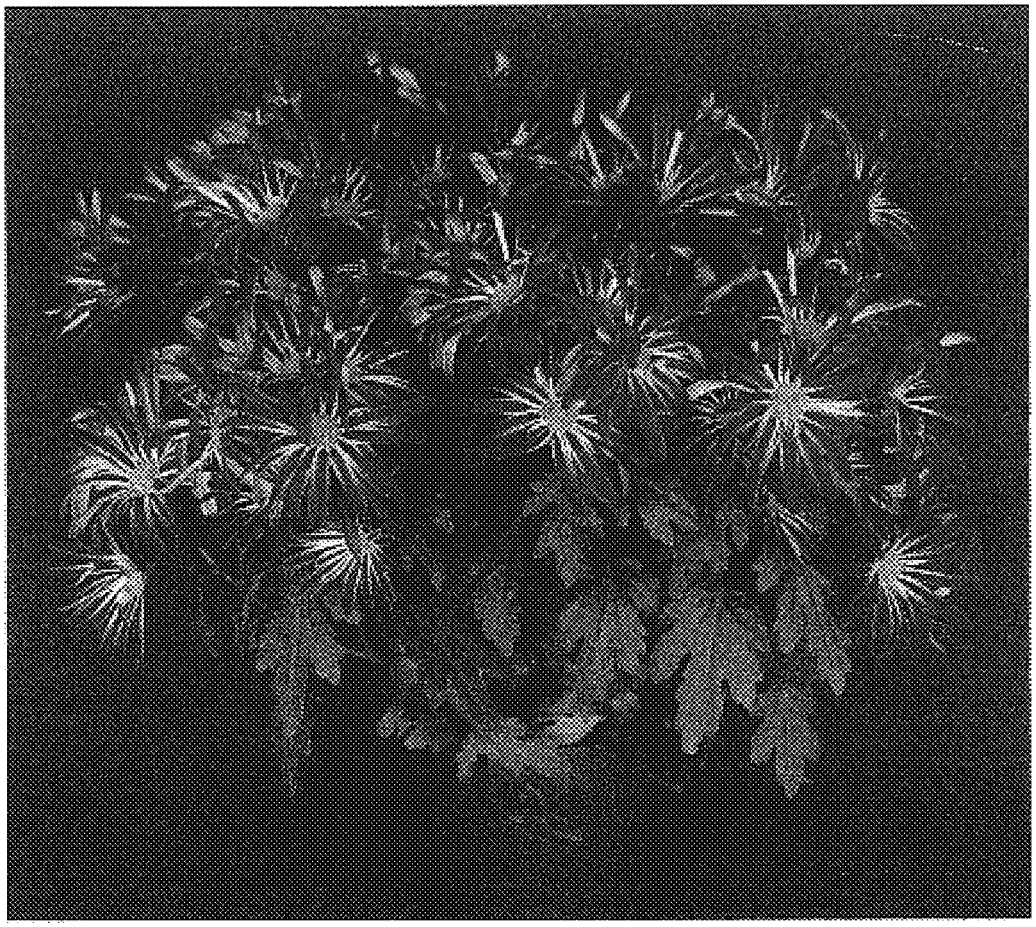

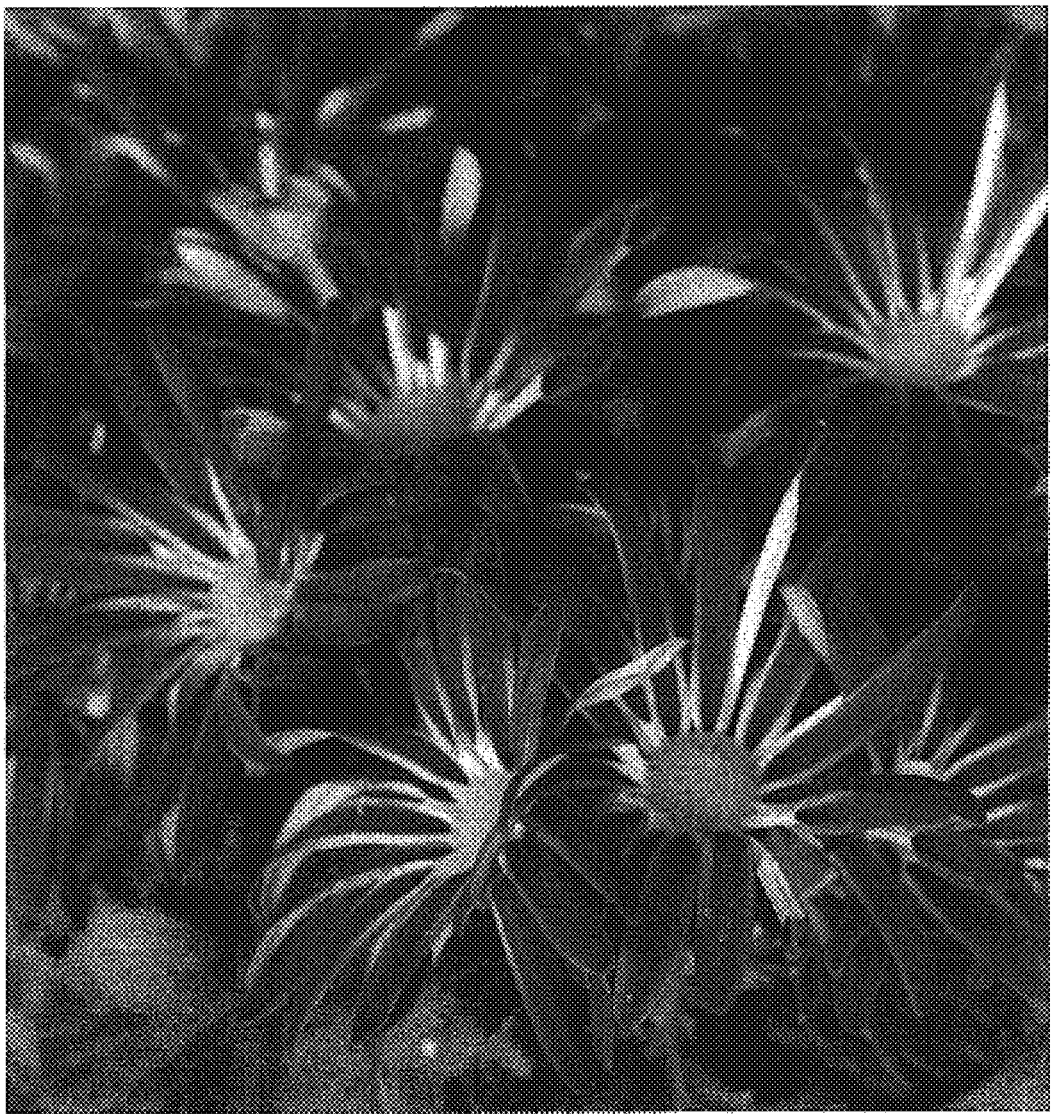

* * * * *